(12) United States Patent
Mincer

(10) Patent No.: US 7,827,894 B2
(45) Date of Patent: Nov. 9, 2010

(54) MICROTOME BLADE

(75) Inventor: Mathew T. Mincer, Oak Park, IL (US)

(73) Assignee: Feather Safety Razor Co., Ltd., Osaka (JP)

( * ) Notice: Subject to any disclaimer, the term of this patent is extended or adjusted under 35 U.S.C. 154(b) by 567 days.

(21) Appl. No.: 11/064,134

(22) Filed: Feb. 23, 2005

(65) Prior Publication Data

US 2006/0185490 A1 Aug. 24, 2006

(51) Int. Cl.
 B26D 7/06 (2006.01)
 B26D 1/00 (2006.01)
 B26B 9/00 (2006.01)
 A61F 9/00 (2006.01)

(52) U.S. Cl. .................... 83/651; 83/915.5; 83/412; 30/346; 606/166

(58) Field of Classification Search ............. 83/412, 83/915.5; 30/51, 346, 346.5, 346.55, 346.61, 30/251, 353, 357; 427/385.5; 606/166, 170, 606/172, 180; 15/236.05
See application file for complete search history.

(56) References Cited

U.S. PATENT DOCUMENTS

| | | | | |
|---|---|---|---|---|
| 420,232 A | | 1/1890 | Heymeier | |
| 1,399,631 A | | 12/1921 | Lofdahl | |
| 1,865,539 A | | 7/1932 | Pietzsch | |
| 1,971,814 A | * | 8/1934 | Genda | ............ 30/232 |
| 1,998,428 A | | 4/1935 | Huettner | |
| 2,232,940 A | * | 2/1941 | Fender | ............ 30/278 |
| 2,238,425 A | * | 4/1941 | Morris | ............ 30/315 |
| 2,274,815 A | * | 3/1942 | Whann | ............ 30/279.6 |
| 2,558,859 A | * | 7/1951 | Lefkowitz | ............ 30/51 |
| 3,109,237 A | * | 11/1963 | Girouard | ............ 30/346.5 |
| 3,328,877 A | * | 7/1967 | Brown | ............ 30/142 |
| 3,465,437 A | * | 9/1969 | Brown | ............ 30/279.6 |
| 3,956,825 A | * | 5/1976 | Ness | ............ 30/279.6 |
| 4,098,278 A | | 7/1978 | Schwartz | |
| 4,221,222 A | * | 9/1980 | Detsch | ............ 606/132 |
| 4,472,989 A | | 9/1984 | Endo | |
| 4,554,735 A | | 11/1985 | Chen | |
| 4,665,915 A | | 5/1987 | Grollimund | |
| 4,690,139 A | | 9/1987 | Rosenberg | |
| 4,998,347 A | | 3/1991 | Schachter | |
| 5,050,470 A | | 9/1991 | Ward | |
| 5,052,108 A | * | 10/1991 | Yang et al. | ............ 30/123.5 |
| 5,092,210 A | | 3/1992 | Dern | |
| 5,624,451 A | * | 4/1997 | Segal | ............ 606/131 |
| 5,740,708 A | | 4/1998 | Tabone | |
| 5,819,628 A | | 10/1998 | Cogan et al. | |
| 5,857,995 A | * | 1/1999 | Thomas et al. | ............ 604/22 |
| 6,440,143 B2 | | 8/2002 | Kasten | |
| 2001/0003938 A1 | | 6/2001 | Heid | |

(Continued)

FOREIGN PATENT DOCUMENTS

JP 51-134488 11/1976

(Continued)

*Primary Examiner*—Ghassem Alie
*Assistant Examiner*—Bharat C Patel
(74) *Attorney, Agent, or Firm*—Workman Nydegger

(57) ABSTRACT

A microtome blade having a safety portion. The safety portion may include a protective portion spaced from a knife edge and a gripping portion extending outwardly from the protective portion. The protective portion and the gripping portion help reduce unintended knife edge cuts.

16 Claims, 1 Drawing Sheet

U.S. PATENT DOCUMENTS

2004/0225309 A1* 11/2004 Eriksson et al. ............. 606/167
2006/0037201 A1* 2/2006 Rasa et al. ................. 30/279.6

FOREIGN PATENT DOCUMENTS

| | | |
|---|---|---|
| JP | 63-4994 | 2/1988 |
| JP | 3033094 | 1/1997 |
| JP | 2000-009608 | 1/2000 |
| JP | 2000-237992 | 9/2000 |
| JP | 2003-130767 | 5/2003 |

* cited by examiner

MICROTOME BLADE

FIELD OF THE INVENTION

The invention relates to a cutting knife and, more particularly, to a cutting knife for use with a microtome.

BACKGROUND OF THE INVENTION

A microtome is a device used in histological examinations that thinly slices a tissue sample into sections that can be used for microscope examination. To obtain such thinly sliced sections, the microtome usually requires a very sharp knife or blade that moves in a reciprocating motion across the tissue sample, which is often embedded in paraffin or other fixative, or remains fixed and the tissue sample reciprocates across the blade. Typically, the knife or blade may be removed from the microtome because, after repeated use, the blade becomes dull and, therefore, no longer provides cleanly cut, thin sections. As a result, from time to time, a new sharp blade is required to be inserted into the microtome.

The typical microtome blade is optimized for cutting. That is, the common microtome blade is generally an elongate structure that has at least one knife edge that extends the entire length of the blade. In many cases, the common microtome blade has two knife edges on opposite sides of the blade where each knife edge extends the entire length of the blade. In such configurations, the knife edges are exposed to the user of the microtome both during the cutting operation and during the eventual replacement of the blade. For instance, in common microtomes, the user is required to retrieve the cut section from the blade after the reciprocating motion, which exposes the users fingers and hands to the knife edge. Additionally, during blade replacement, the user must handle the blade directly, which also exposes the users fingers and hands to the knife edge. As a result, unintended injuries, such as finger and hand cuts, are possible if the user is not careful, not paying attention, or not experienced with the use of the microtome.

In a laboratory setting, where a microtome is most often used, preventing unintended knife cuts or sharp-object injuries (i.e., sharps' injuries) is of primary importance. However, due to the configuration of typical microtome blades, such as exposed knife edges that extend the length of the blade, unintended cuts during microtome use or blade replacement are frequently encountered in laboratories utilizing microtomes. Attempts to eliminate such unintended cuts generally center around effective training or providing supplemental protective equipment. However, such solutions have shortcomings.

Effective training and safe working procedures are often the first step undertaken by laboratories using microtomes to prevent unintended blade cuts. Such training and procedures often includes education on proper handling of blades, safe procedures for insertion of the blade in the microtome, and safe procedures for operation of the microtome. However, improved training, education, and attention to safe working practices do not eliminate all unintended microtome knife cuts. Often the laboratory worker is rushed, believes that such procedures are unnecessary, or fails to pay attention to a routine procedure that is performed safely many times.

Other attempts at preventing unintended blade cuts involve providing supplemental protective equipment. Such equipment may include special gloves or knife protectors. For example, cut resistant gloves are one type of supplemental protective equipment. However, such gloves may create other unwanted problems. For instance, the user may lose tactile feel with the gloves, which may make it difficult to retrieve the cut sections. Furthermore, the gloves may be bulky, which may complicate the blade replacement procedures. Knife protectors, on the other hand, are another type of supplemental protective equipment. Such protectors typically involve a blade holder or other structure on the microtome itself that includes a safety surface that guards the knife edge. For instance, U.S. Pat. Nos. 1,998,428; 5,092,210; and 5,740,708 are typical microtome blade holders that include examples of protective surfaces. However, such protections also may create other unwanted issues. Such knife protectors are often bulky, require additional assembly steps to install the blade, complicate the operation of the microtome, and involve additional expense to the laboratory.

Consequently, it is desired to obtain a microtome blade having simple safety features to reduce unintended knife cuts that do not hinder the use of the microtome or complicate the blade replacement procedures.

SUMMARY OF THE INVENTION

The invention relates to a microtome blade having a safety portion to help reduce unintended blade cuts. In a preferred form, the safety portion may include a protective portion and a gripping portion, but other safety features or other combinations of these features are possible.

In one aspect, the microtome blade may include a blade portion having a knife edge in a cutting direction and spaced from the knife edge in the cutting direction may be the protective portion. The protective portion helps reduce unintended knife edge cuts by providing a surface that a user's hand or finger will contact prior to the knife edge. The microtome blade may also include a pair of connecting or bridge portions that extend outwardly from the blade portion that join the protective portion to the blade portion. In such configuration, a space may be formed between the protective portion and the blade portion.

As mentioned above, the microtome blade may also include the gripping portion. If included, the gripping portion generally extends outwardly from at least one of the connecting or bridge portions in the cutting direction. The gripping portion preferably provides a surface for handling that is away from the knife edge.

In one form, the protective portion and the gripping portion taper or angle outwardly from the blade portion. In other forms, the blade portion may be in a first plane and the protective portion may be in a second plane such that the protective portion does not interfere with the knife edge during cutting. In yet another form, the first plane and the second plane are skewed.

DESCRIPTION OF THE PREFERRED EMBODIMENTS

Figure 1:
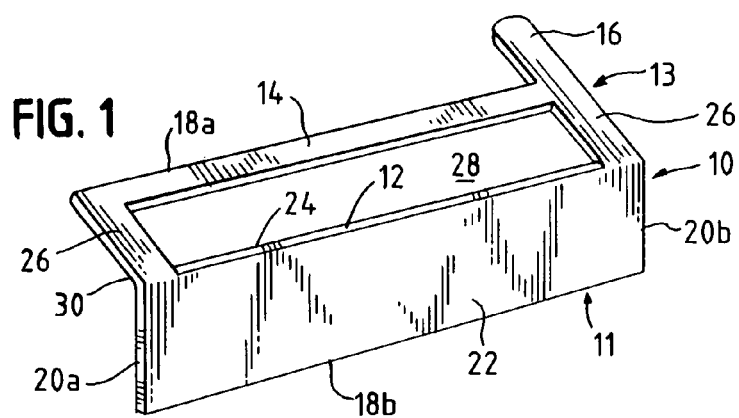
FIG. 1 is a perspective view of an exemplary microtome blade embodying safety features.
Figure 2:
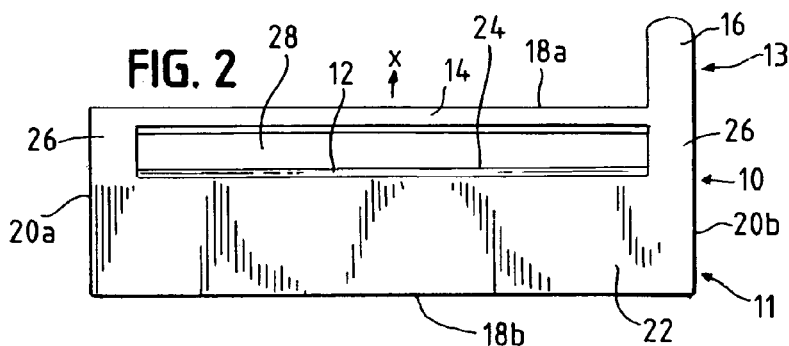
FIG. 2 is a front elevational view of the microtome blade of FIG. 1.
Figure 3:
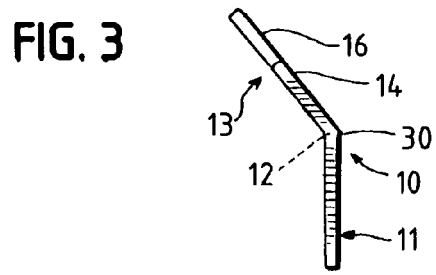
FIG. 3 is a side elevational view of the microtome blade of FIG. 1.

Referring to FIGS. 1-3, an exemplary microtome or cutting blade 10 that includes safety features is illustrated. In general, the exemplary blade 10 includes a body or blade portion 11 and a safety portion 13. The body portion 11 generally includes a main portion 22 and a cutting portion 12. The safety portion 13, in a preferred embodiment, includes a protective portion 14 and a gripping portion 16. In such preferred embodiment, the protective portion 14 is spaced from the cutting portion 12 such that when the blade 10 is installed on a microtome, the protective portion 14 provides a protective surface that a users fingers would contact before engaging the cutting portion 12. Similarly, the gripping portion 16 provides a surface away from the cutting portion 12 that a user may hold during blade replacement procedures. As a result, both the protective portion 14 and the gripping portion 16 help reduce unintended blade cuts.

More specifically, blade 10 has an generally elongate body that is sized to be installed on a typical microtome. The body of blade 10 is defined by a pair of spaced side edges 18a and 18b, which provide a length, and a pair of spaced end edges 20a and 20b, which provide a width. Blade 10 may be constructed out of steel or stainless steel, but may also be any other material suitable for use in slicing tissue samples that is known in the art. As will be more further described below, it is preferred that the safety portion 13 is angled or tapered away from the body portion 11.

The body portion 11 includes features of a traditional microtome blade. As discussed above, the body portion 11 generally includes the main portion 22 and the cutting portion 12. The main portion 22 is generally defined by side edge 18b, a portion of both end edges 20a and 20b, and the cutting portion 12. The main portion 22 is receivable in a typical blade holder of a microtome in a known manner and is sized accordingly. The cutting portion 12, in this embodiment, is disposed internally of the body of blade 10 and is for slicing the tissue sections in a known manner. Accordingly, the cutting portion 12 terminates in a knife edge 24; that is, the cutting portion 12 tapers downward to a sharp edge that faces a cutting direction as shown by the arrow X.

The safety portion 13 is a feature not found on traditional microtome blades. In this embodiment, the safety portion 13 extends away from the body portion 11 in the cutting direction X. The safety portion 13, in a preferred form, includes the protective portion 14, the gripping portion 16, and a pair of bridge portions 26, which join the protective portion 14 to the body portion 11. The bridge portions 26 are disposed at distal ends of the blade 10 along each end edge 20a and 20b and extend between the body portion 11 and the protective portion 14 such that a space 28 is formed between the cutting portion 12 and the safety portion 14. The space 28 is preferably sized to be much smaller than the width of a finger so that a user's finger cannot be inserted under the safety portion 14 to contact the knife edge 24. The protective portion 14, which may be a strip, a rail, or other elongate structure along the side edge 18a, extends between the distal bridge portions 26 and is, therefore, spaced from the cutting portion 12 in the cutting direction X. The protective portion 14 provides a surface that a user's fingers or hand will contact prior to contacting the cutting portion 12. In this embodiment, the gripping portion 16, which may be a tab or other suitable projection, extends outwardly from the protective portion 14 and may be aligned with one of the bridge portions 26 along the end edge 20b. The gripping portion 16 is sized for ease of handling so that a user may comfortably grip the blade 10 between an index finger and a thumb and provides a surface for handling away from the cutting portion 12.

Preferably, the safety portion 13 is angled away from the body portion 11. As best illustrated in FIGS. 1 and 3, the body of blade 10 is bent or angled at portion 30 so that the safety portion 13 tapers away from the body portion 11. In such preferred configuration, when installed on a typical microtome, the safety portion 13 is angled outwardly, toward the user and away from the microtome. In this manner, the safety portion 13 does not interfere with the cutting of sections on the microtome, but, as described above, provides a surface that guards the knife edge 24. While it is preferred to angle the safety portion 13 away from the body portion 11 such that these portions are in different planes or skewed toward each other, it is also possible to have portions 11 and 13 co-planar. In this alternative configuration, it may be preferable to have the safety portion 13 to be more flexible or thinner than the body portion 11 so that the safety portion 13 flexes or bends away from the tissue sample during cutting.

Figure 4:
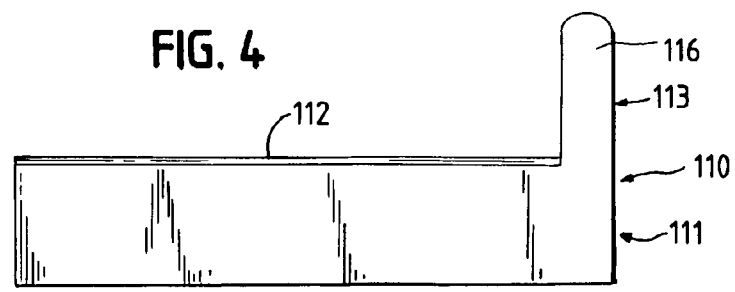
FIG. 4 is a front elevational view of an alternative microtome blade embodying safety features.
Figure 5:
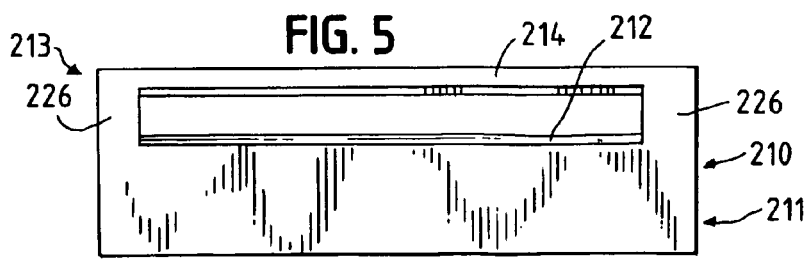
FIG. 5 is a front elevational view of another alternative microtome blade embodying safety features.

Referring to FIGS. 4 and 5, alternative embodiments of the microtome blade are illustrated having different combinations of the safety features. For example, FIG. 4 illustrates blade 110, which also includes a blade portion 111 and a safety portion 113, but only includes a gripping portion 116 in the safety portion 113. The gripping portion 116 is similar to the gripping portion 16. In this embodiment, the gripping portion 116 is disposed on a distal end of the blade 110 and extends outwardly away from a cutting portion 112, which is on an edge of the blade portion 111. The gripping portion 116 is a tab or other extension suitable for holding the blade 110 between a user's index finger and thumb. As with the first embodiment, the safety portion 113 may be tapered or angled away from the blade portion 111.

FIG. 5, on the other hand, illustrates blade 210, which also has a blade portion 211 and a safety portion 213, but this embodiment only includes a protective portion 214 in the safety portion 213. The protective portion 214 is equivalent to the protective portion 14 and is spaced from a cutting portion 212 similar to the first embodiment. As with blade 10, the protective portion 214 may be a rail, a strip, or other elongate structure that is spaced from the cutting portion 212 in a cutting direction and extends between spaced bridge portions 226, which extend outwardly from the blade portion 211 on distal ends of the blade 210. As with the protective portion 14 on the blade 10, the protective portion 214 provides a surface that a user's fingers or hand would contact prior to contacting the cutting portion 212; therefore, reducing unintended cuts. As with the other embodiments, the safety portion 213 may be tapered or angled away from the blade portion 211.

It will be understood that various changes in the details, materials, and arrangements of parts and components, which have been herein described and illustrated in order to explain the nature of the invention may be made by those skilled in the art within the principle and scope of the invention as expressed in the appended claims.

What is claimed is:

1. A microtome blade comprising:
a blade portion having a knife edge in a cutting direction, the blade portion being defined by the knife edge, a side edge and a pair of end edges;
a protective portion spaced from the knife edge in the cutting direction, the protective portion to reduce unintended knife edge cuts;
a pair of connecting portions extending outwardly from distal ends of the blade portion joining the protective portion to the blade portion;
a space between the protective portion and the knife edge; and
a gripping portion extending outwardly from one side of at least one connecting, portion in the cutting direction, wherein the gripping portion provides a surface for handling away from the cutting portion, wherein the gripping portion is aligned with one of the connecting portions along one of the end edges of the blade portion, and wherein the blade portion is in a first flat plane and the protective portion, the connecting portions, and the gripping portion are in a second flat plane, wherein the first plane and the second plane are angled with respect to each other by approximately 140 degrees, wherein the protective portion and the gripping portion taper outwardly from the blade portion at the angle, and wherein the space has a pair of first and second inner edges facing each other, the first inner edge is formed at the blade portion, and the second inner edge is formed at the protective portion, the first inner edge corresponds to the knife edge.

2. A cutting blade for use with a microtome, the cutting blade comprising: an elongate body having spaced first and second sides along a length; a cutting portion on the elongate body spaced inward from the first side and having a knife edge in a cutting direction; and a protective portion on the elongate body adjacent the first side and spaced from the knife edge in the cutting direction to reduce unintended knife-edge cuts.

3. The cutting blade of claim 2, further comprising a gripping portion extending outwardly from the first side in the cutting direction to provide a surface for handling away from the cutting portion.

4. The cutting blade of claim 3, wherein the gripping portion is a tab.

5. The cutting blade of claim 2, wherein the cutting portion is in a first plane and the protective portion is in a second, different plane such that the protective portion does not interfere with the knife edge during cutting.

6. The cutting blade of claim 5, wherein the first and second planes are skewed.

7. The cutting blade of claim 2, wherein the protective portion is a strip extending along the first side.

8. A cutting blade for use with a microtome, the cutting blade comprising: an elongate body having a cutting edge along a length and spaced first and second ends along a width; a cutting portion on the cutting edge having a knife edge in a cutting direction; and a gripping portion adjacent the first end extending outwardly from the cutting edge in the cutting direction to provide a surface for handling away from the cutting portion.

9. The cutting blade of claim 8, further comprising a protective portion spaced from the cutting edge in the cutting direction to reduce unintended knife edge cuts.

10. The cutting blade of claim 9, wherein the protective portion is in a first plane and the cutting portion is in a second, different plane such that the protective portion does not interfere with the knife edge during cutting.

11. The cutting blade of claim 10, wherein the first plane and the second plane are skewed.

12. The cutting blade of claim 9, wherein the protective portion is a strip extending along the cutting edge.

13. The microtome blade of claim 1, wherein the space between the protective portion and the knife edge is sized to be much smaller than a width of a finger of a user.

14. The microtome blade of claim 1, wherein the microtome blade is constructed out of steel and bent at the pair of the connecting portions.

15. The microtome blade of claim 1, wherein the gripping portion is a tab that has substantially the same width as that of the connecting portion.

16. The microtome blade of claim 1, wherein the microtome blade is formed from one piece of a material.

\* \* \* \* \*